US007109323B2

(12) United States Patent
Plamondon et al.

(10) Patent No.: US 7,109,323 B2
(45) Date of Patent: Sep. 19, 2006

(54) FORMULATION OF BORONIC ACID COMPOUNDS

(75) Inventors: Louis Plamondon, Watertown, MA (US); Louis Grenier, Cambridge, MA (US); Julian Adams, Brookline, MA (US); Shanker Lal Gupta, Rockville, MD (US)

(73) Assignees: The United States of America as represented by the Department of Health and Human Services, Washington, DC (US); Millennium Pharmaceutical, Inc., Cambridge, MA (US)

( * ) Notice: Subject to any disclaimer, the term of this patent is extended or adjusted under 35 U.S.C. 154(b) by 245 days.

(21) Appl. No.: 10/744,843

(22) Filed: Dec. 23, 2003

(65) Prior Publication Data

US 2004/0138411 A1 Jul. 15, 2004

Related U.S. Application Data

(63) Continuation of application No. 10/056,563, filed on Jan. 25, 2002, now Pat. No. 6,699,835.
(60) Provisional application No. 60/264,160, filed on Jan. 25, 2001.

(51) Int. Cl.
*C07H 3/00* (2006.01)
*A61K 38/00* (2006.01)
*A61K 33/22* (2006.01)
*C07K 9/00* (2006.01)
*C07F 5/02* (2006.01)

(52) U.S. Cl. .................... 536/53; 536/17.1; 514/2; 514/18; 514/19; 514/64; 544/229; 530/320
(58) Field of Classification Search ............ 536/53, 536/17.1; 514/2, 18, 19, 64; 544/229; 530/320; 558/286
See application file for complete search history.

(56) References Cited

U.S. PATENT DOCUMENTS

| | | | |
|---|---|---|---|
| 4,499,082 | A | 2/1985 | Shenvi et al. |
| 5,106,948 | A | 4/1992 | Kinder et al. |
| 5,169,841 | A | 12/1992 | Kleeman et al. |
| 5,187,157 | A | 2/1993 | Kettner et al. |
| 5,242,904 | A | 9/1993 | Kettner et al. |
| 5,250,720 | A | 10/1993 | Kettner et al. |
| 5,492,900 | A | 2/1996 | LaHann |
| 5,574,017 | A | 11/1996 | Gutheil |
| 5,780,454 | A | 7/1998 | Adams et al. |
| 5,935,944 | A | 8/1999 | LaHann |
| 5,990,083 | A | 11/1999 | Iqbal et al. |
| 6,066,730 | A | 5/2000 | Adams et al. |
| 6,083,903 | A | 7/2000 | Adams et al. |
| 6,169,076 | B1 | 1/2001 | Shull et al. |
| 6,297,217 | B1 | 10/2001 | Adams et al. |
| 6,699,835 | B1 * | 3/2004 | Plamondon et al. ........... 514/2 |
| 6,713,446 | B1 * | 3/2004 | Gupta ........................... 514/2 |
| 2002/0169114 | A1 | 11/2002 | Gupta |

FOREIGN PATENT DOCUMENTS

| | | |
|---|---|---|
| WO | WO 98/35691 A1 | 8/1998 |
| WO | WO 99/15183 A1 | 4/1999 |
| WO | WO 00/57887 A1 | 10/2000 |
| WO | WO 01/02424 A2 | 1/2001 |
| WO | WO 02/059130 A1 | 1/2002 |

OTHER PUBLICATIONS

Ciechanover, "The Ubiquitin–Proteasome Proteolytic Pathway," *Cell*, vol. 79, pp. 13–21 (Oct. 7, 1994).
Gennaro, "Remington: The Science and Practice of Pharmacy," $20^{th}$ Edition, Chapter 42, pp. 802–803 (2000).
Kataoka et al., "Totally Synthetic Polymer Gels Responding to External Glucose Concentration: Their Preparation and Application to On–Off Regulations of Insulin Release," *J. Am. Chem. Soc.*, vol. 120, pp. 12694–12695 (1998).
Kibbe, "Handbook of Pharmaceutical Excipients," $3^{rd}$ Edition, pp. 324–328 (2000).
Korcek et al., "Absolute Rate Constants for the Autoxidation of Organometallic Compounds, Part II. Benzylboranes and 1–Phenylethylboranes," *J. Chem. Soc., Perkin Trans.* II, pp. 242–248 (1972).
Richardson et al., "A Phase 2 Study of Bortezomib in Relapsed, Refractory Myeloma," *N. Engl. J. Med.*, vol. 348, No. 26, pp. 2609–2617 (1958).
Snyder et al., "Aryl Boronic Acids. II. Aryl Boronic Anhydrides and their Amine Complexes," *J. Am. Chem. Soc.*, vol. 80, pp. 3611–3615 (1958).
Stella et al., "Development of Parenteral Formulations of Experimental Cytoxic Agents. I. Rhizoxin (NSC–332598)," *International Journal of Pharmaceutics*, vol. 43, pp. 191–199 (1988).
Williams et al., "The Effects of Cooling Rate on Solid Phase Transitions and Associated Vial Breakage Occuring in Frozen Mannitol Solutions," *Journal of Parenteral Science & Technology*, vol. 40, No. 4, pp. 135–141 (Jul. –Aug. 1986).
Williams et al., "Vial Breakage by Frozen Mannitol Solutions: Correlation with Thermal Characteristics and Effect of Stereoisomerism, Additives, and Vial Configuration," *Journal of Parenteral Science & Technology* vol. 45, No. 2, pp. 94–100 (Mar.–Apr. 1991).

* cited by examiner

*Primary Examiner*—James O. Wilson
*Assistant Examiner*—Michael C. Henry
(74) *Attorney, Agent, or Firm*—Leydig, Voit & Mayer, Ltd.

(57) ABSTRACT

The invention relates to the formulation of pharmaceutical compounds. More particularly, the invention provides stable, pharmaceutically acceptable compositions prepared from boronic acid compounds and methods for preparing the compositions. The invention also provides novel boronate ester compounds. The invention further provides boronic acid anhydride compounds useful in the methods of the invention.

12 Claims, No Drawings

FORMULATION OF BORONIC ACID COMPOUNDS

CROSS-REFERENCE TO RELATED APPLICATIONS

This patent application is a continuation of U.S. patent application No. 10/056,563, now U.S. patent 6,699,835, filed Jan. 25, 2002 which claims the benefit of U.S. Provisional Patent Application No. 60/264,160, filed Jan. 25, 2001.

GOVERNMENT FUNDING

Work described herein was performed under Collaborative Research and Development Agreement (CRADA) Number 0676. The United States Government has certain rights in the invention.

BACKGROUND OF THE INVENTION

1. Field of the Invention

This invention relates to the formulation of pharmaceutical compounds. More particularly, the invention relates to stable, pharmaceutically acceptable compositions prepared from boronic acid compounds. The invention also relates to methods for preparing such compositions.

2. Summary of the Related Art

Boronic acid and ester compounds display a variety of pharmaceutically useful biological activities. Shenvi et al., U.S. Pat. No. 4,499,082 (1985), discloses that peptide boronic acids are inhibitors of certain proteolytic enzymes. Kettner and Shenvi, U.S. Pat. No. 5,187,157 (1993); U.S. Pat. No. 5,242,904 (1993); and U.S. Pat. No. 5,250,720 (1993), describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain tripeptide boronic acid compounds inhibit the growth of cancer cells.

More recently, boronic acid and ester compounds have displayed particular promise as inhibitors of the proteasome, a multicatalytic protease responsible for the majority of intracellular protein turnover. Ciechanover, Cell, 79: 13–21 (1994), teaches that the proteasome is the proteolytic component of the ubiquitin-proteasome pathway, in which proteins are targeted for degradation by conjugation to multiple molecules of ubiquitin. Ciechanover also teaches that the ubiquitin-proteasome pathway plays a key role in a variety of important physiological processes.

Adams et al., U.S. Pat. No. 5,780,454 (1998), U.S. Pat. No. 6,066,730 (2000), U.S. Pat. No. 6,083,903 (2000), and U.S. Pat. No. 6,297,217 (2001), hereby incorporated by reference in their entirety, describe peptide boronic ester and acid compounds useful as proteasome inhibitors. The references also describe the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, to inhibit antigen presentation in a cell, to inhibit NF-κB dependent cell adhesion, and to inhibit HIV replication. Brand et al., WO 98/35691, teaches that proteasome inhibitors, including boronic acid compounds, are useful for treating infarcts such as occur during stroke or myocardial infarction. Elliott et al., WO 99/15183, teaches that proteasome inhibitors are useful for treating inflammatory and autoimmune diseases.

Unfortunately, alkylboronic acids are relatively difficult to obtain in analytically pure form. For example, Snyder et al., J. Am. Chem. Soc. 80: 3611 (1958), teaches that arylboronic acid compounds readily form cyclic trimeric anhydrides under dehydrating conditions. Also, alkylboronic acids and their boroxines are often air-sensitive. Korcek et al., J. Chem. Soc., Perkin Trans. 2 242 (1972), teaches that butylboronic acid is readily oxidized by air to generate 1-butanol and boric acid. These difficulties limit the pharmaceutical utility of boronic acid compounds, complicating the characterization of pharmaceutical agents comprising boronic acid compounds and limiting their shelf-life.

There is thus a need in the art for improved formulations of boronic acid compounds. Ideally, such formulations would be conveniently prepared, would exhibit enhanced stability and longer shelf life as compared to the free boronic acid compound, and would readily liberate the bioactive boronic acid compound when administered to a subject in need of boronic acid therapy.

SUMMARY OF THE INVENTION

The present invention provides stable, pharmaceutically acceptable compositions prepared from boronic acid compounds. The invention also provides methods for preparing such compositions. The invention provides the discovery that lyophilization of an aqueous mixture comprising a boronic acid compound and a compound having at least two hydroxyl groups produces a stable composition that readily releases the boronic acid compound upon dissolution in aqueous media.

In a first aspect, the invention provides boronate ester compounds having formula (1):

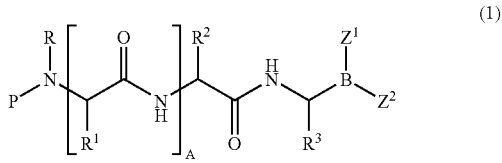

P is hydrogen or an amino-group protecting moiety;

R is hydrogen or alkyl;

A is 0, 1, or 2;

$R^1$, $R^2$, and $R^3$ are independently hydrogen, alkyl, cycloalkyl, aryl, or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^1$ and $Z^2$ together form a moiety derived from a sugar, wherein the atom attached to boron in each case is an oxygen atom.

In a second aspect, the invention provides a composition comprising a compound of formula (2):

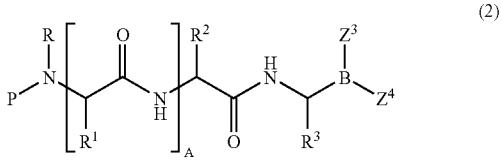

(2)

wherein:
P is hydrogen or an amino-group-protecting moiety;
R is hydrogen or alkyl;
A is 0, 1, or 2;
$R^1$, $R^2$, and $R^3$ are independently hydrogen, alkyl, cycloalkyl, aryl, or —$CH_2$—$R^5$;
$R^5$, in each instance, is one of aryl, aralkyl, alkaryl, cycloalkyl, heterocyclyl, heteroaryl, or —W—$R^6$, where W is a chalcogen and $R^6$ is alkyl;
where the ring portion of any of said aryl, aralkyl, alkaryl, cycloalkyl, heterocyclyl, or heteroaryl in $R^1$, $R^2$, $R^3$ or $R^5$ can be optionally substituted; and
$Z^3$ and $Z^4$ together form a moiety derived from a compound having at least two hydroxyl groups separated by at least two connecting atoms in a chain or ring, said chain or ring comprising carbon atoms and, optionally, a heteroatom or heteroatoms which can be N, S, or O;
in a lyophilized powder.

In a third aspect, the invention provides a method for formulating a boronic acid compound, the method comprising:
(a) preparing an aqueous mixture comprising
  (i) a boronic acid compound; and
  (ii) a compound having at least two hydroxyl groups separated by at least two connecting atoms in a chain or ring, the chain or ring comprising carbon atoms, and optionally, a heteroatom or heteroatoms which can be N, S, or O; and
(b) lyophilizing the mixture.

In a fourth aspect, the invention provides a method for formulating a boronic acid compound, the method comprising:
(a) preparing a boronic acid anhydride compound;
(b) mixing the boronic acid anhydride compound with water and a compound having at least two hydroxyl groups separated by at least two connecting atoms in a chain or ring, the chain or ring comprising carbon atoms, and, optionally, a heteroatom or heteroatoms which can be N, S, or O to produce an aqueous mixture; and
(c) lyophilizing the mixture.

In a fifth aspect, the invention provides compositions prepared by the methods of the invention.

In a sixth aspect, the invention provides boronic acid anhydride compounds useful in the methods of the invention.

DESCRIPTION OF THE PREFERRED EMBODIMENTS

The invention provides stable, pharmaceutically acceptable compositions prepared from boronic acid compounds and methods for preparing the compositions. The invention also provides novel boronate ester compounds. The invention further provides boronic acid anhydride compounds useful in the methods of the invention.

The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used:

As used herein, the terms "formulate" and "formulation" refer to the preparation of a boronic acid compound in a form suitable for administration to a mammalian subject, preferably a human. Often, formulation of the boronic acid compound comprises addition of pharmaceutically acceptable excipients, diluents, or carriers. In some embodiments, formulation of the boronic acid compound comprises formation of a chemical derivative of the boronic acid compound, preferably formation of a boronate ester. The term "formulation" refers to any form commonly used for pharmaceutical administration, including solids, liquids, suspensions, creams, and gels. For purposes of the present invention, the formulation is preferably a lyophilized powder.

As used herein, the term "lyophilized powder" refers to any solid material obtained by lyophilization of an aqueous mixture.

By "stable formulation" is meant any formulation having sufficient stability to have utility as a pharmaceutical agent. Preferably, the formulation has sufficient stability to allow storage at a convenient temperature, preferably between 0° C. and 40° C., for a reasonable period of time, preferably longer than one month, more preferably longer than three months, even more preferably longer than six months, and most preferably longer than one year.

As employed herein, the term "boronic acid" refers to any chemical compound comprising a —$B(OH)_2$ moiety. Snyder et al., *J. Am. Chem. Soc.* 80: 3611 (1958), teaches that arylboronic acid compounds readily form oligomeric anhydrides by dehydration of the boronic acid moiety. Thus, unless otherwise apparent from context, the term "boronic acid" is expressly intended to encompass free boronic acids, oligomeric anhydrides, including, but not limited to, dimers, trimers, and tetramers, and mixtures thereof.

As employed herein, the term "compound having at least two hydroxyl groups" refers to any compound having two or more hydroxyl groups. For purposes of the present invention, the two hydroxyl groups are preferably separated by at least two connecting atoms, preferably from about 2 to about 5 connecting atoms, more preferably 2 or 3 connecting atoms. The connecting atoms may be in a chain or a ring, the chain or ring comprising carbon atoms and, optionally, a heteroatom or heteroatoms which can be N, S, or O. For convenience, the term "dihydroxy compound" may be used to refer to a compound having at least two hydroxyl groups, as defined above. Thus, as employed herein, the term "dihydroxy compound" is not intended to be limited to compounds having only two hydroxyl groups.

As employed herein, the term "amino-group protecting moiety" refers to any group used to derivatize an amino group, especially an N-terminal amino group of a peptide or amino acid. Such groups include, without limitation, alkyl, acyl, alkoxycarbonyl, aminocarbonyl, and sulfonyl moieties. However, the term "amino-group protecting moiety" is not intended to be limited to those particular protecting groups that are commonly employed in organic synthesis, nor is it intended to be limited to groups that are readily cleavable.

The term "chalcogen" as employed herein refers to the elements oxygen or sulfur.

The term "alkyl" as employed herein refers to straight and branched chain aliphatic groups having from 1 to 12 carbon atoms, preferably 1–8 carbon atoms, more preferably 1–6 carbon atoms, and still more preferably 1–4 carbon atoms, which may be optionally substituted with one, two or three substituents. Unless otherwise explicitly stated, the term "alkyl" is meant to include saturated, unsaturated, and partially unsaturated aliphatic groups. When unsaturated groups are particularly intended, the terms "alkenyl" or "alkynyl" will be used. When only saturated groups are intended, the term "saturated alkyl" will be used. Preferred saturated alkyl groups include, without limitation, methyl, ethyl, propyl, isopropyl, butyl, isobutyl, sec-butyl, tert-butyl, pentyl, and hexyl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a $C_6$–$C_{14}$ aromatic moiety comprising one to three aromatic rings, which may be optionally substituted. Preferably, the aryl group is a $C_6$–$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $(C_1$–$C_6)$alk$(C_6$–$C_{10})$aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methylnaphthyl.

The terms "heterocycle", "heterocyclic", and "heterocyclyl" refer to any stable ring structure having from about 3 to about 8 atoms, wherein one or more atoms are selected from the group consisting of N, O, and S. The nitrogen and sulfur heteroatoms of the heterocyclic moiety may be optionally oxidized, and the nitrogen atoms may be optionally quaternized. The heterocyclic ring can be attached to its pendant group at any heteroatom or carbon atom that results in a stable formula. The term "stable compound" or "stable formula" is meant to refer to a compound that is sufficiently robust to survive isolation to a useful degree of purity from a reaction mixture and formulation into an efficacious therapeutic agent.

The heterocyclic group may be optionally substituted on carbon at one or more positions with any of the substituents recited above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, oxo, or hydroxy, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholinyl. The heterocyclic group may also be fused to an aryl, heteroaryl, or heterocyclic group. Examples of such fused heterocyles include, without limitation, tetrahydroquinoline and dihydrobenzofuran.

As used herein, the terms "heteroaryl" and "aromatic heterocycle" refer to groups having 5 to 14 ring atoms, preferably 5, 6, 9, or 10 ring atoms; having 6, 10, or 14 π electrons shared in a cyclic array; and having, in addition to carbon atoms, from one to about four, preferably from one to about three, heteroatoms selected from the group consisting of N, O, and S. The heteroaryl group may be optionally substituted on carbon at one or more positions with any of the substituents recited above. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

As employed herein, a "substituted" alkyl, cycloalkyl, aryl, heterocyclyl, or heteroaryl group is one having from one and to about four, preferably from one to about three, more preferably one or two, non-hydrogen substituents. Suitable substituents include, without limitation, halo, hydroxy, oxo, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferably the substituents are independently selected from the group consisting of $C_1$–$C_6$ alkyl, $C_3$–$C_8$ cycloalkyl, $(C_1$–$C_6)$ alkyl $(C_3$–$C_8)$cycloalkyl, $C_2$–$C_8$alkenyl, $C_2$–$C_8$ alkynyl, cyano, amino, $C_1$–$C_6$alkylamino, di$(C_1$–$C_6)$ alkylamino, benzylamino, dibenzylamino, nitro, carboxy, carbo$(C_1$–$C_6)$ alkoxy, trifluoromethyl, halogen, $C_1$–$C_6$ alkoxy, $C_6$–$C_{10}$ aryl, $(C_6$–$C_{10})$aryl$(C_1$–$C_6)$alkyl, $(C_6$–$C_{10})$aryl$(C_1$–$C_6)$ alkoxy, hydroxy, $C_1$–$C_6$ alkylthio, $C_1$–$C_6$ alkylsulfinyl, $C_1$–$C_6$ alkylsulfonyl, $C_6$–$C_{10}$ arylthio, $C_6$–$C_{10}$ arylsulfinyl, $C_6$–$C_{10}$ arylsulfonyl, $C_6$–$C_{10}$ aryl, $(C_1$–$C_6)$alkyl $(C_6$–$C_{10})$ aryl, and halo$(C_6$–$C_{10})$aryl.

The term "halogen" or "halo" as employed herein refers to chlorine, bromine, fluorine, or iodine.

The term oxo refers to an oxygen atom, which forms a carbonyl when attached to carbon, an N-oxide when attached to nitrogen, and a sulfoxide or sulfone when attached to sulfur.

As herein employed, the term "acyl" refers to an alkylcarbonyl or arylcarbonyl substituent.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. The term "amino" is meant to include $NH_2$, alkylamino, arylamino, and cyclic amino groups.

The term "ureido" as employed herein refers to a substituted or unsubstituted urea moiety.

In a first aspect, the invention provides boronate ester compounds having formula (1):

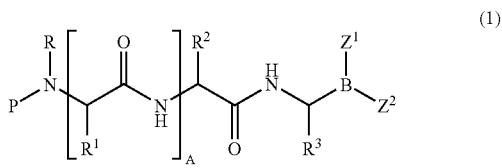

(1)

wherein

P is hydrogen or an amino-group protecting moiety;

R is hydrogen or alkyl;

A is 0, 1, or 2;

$R^1$, $R^2$, and $R^3$ are independently hydrogen, alkyl, cycloalkyl, aryl, or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^1$ and $Z^2$ together form a moiety derived from a sugar, wherein the atom attached to boron in each case is an oxygen atom.

As used herein, the term "moiety derived from a sugar" refers to a moiety formed by removing the hydrogen atoms from two hydroxyl groups of any sugar moiety. The moiety derived from a sugar may be attached to boron by any two of the hydroxyl groups of the sugar. For example, in various embodiments, the boronate ester forms a 5-, 6-, 7-, 8-, or 9-membered ring. In some preferred embodiments, the boronate ester forms a 5- or 6-membered ring.

The sugar is preferably a monosaccharide or disaccharide. Non-limiting examples of suitable sugars include, glucose, sucrose, fructose, trehalose, mannitol, and sorbitol. In certain preferred embodiments, the sugar is a reduced sugar, more preferably mannitol or sorbitol. Thus, in the embodiment wherein the sugar is mannitol or sorbitol, $Z^1$ and $Z^2$ together form a moiety of formula $C_6H_{12}O_6$, wherein the oxygen atoms of the two deprotonated hydroxyl groups form covalent attachments with boron to form a boronate ester compound.

Preferably, the mannitol or sorbitol boronate ester compound has one of the following structures:

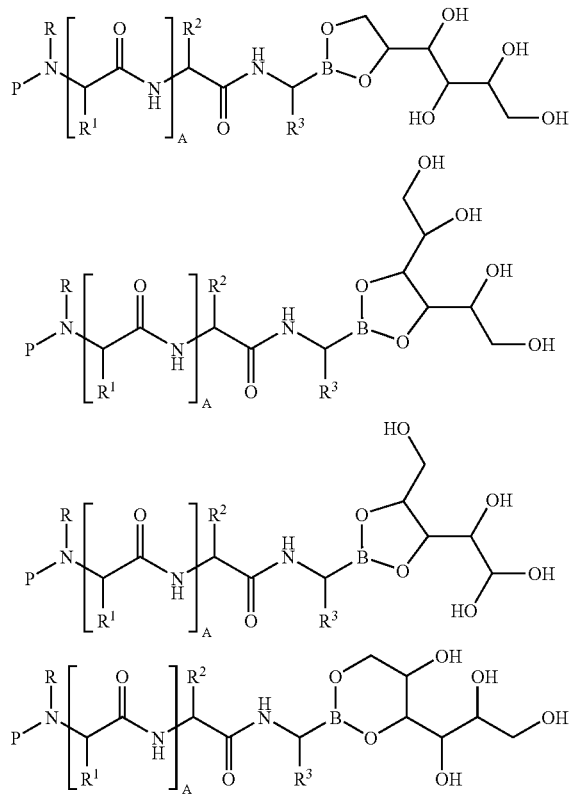

However, structures with larger boronate ester ring sizes are also possible.

In certain preferred embodiments, the mannitol or sorbitol boronate ester forms a symmetrical 5-membered ring having the following structure:

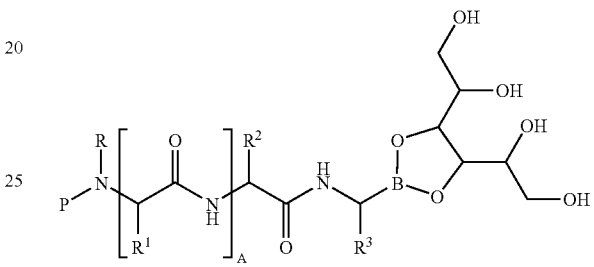

Preferably, the mannitol or sorbitol is of the D-configuration, although the L-configuration may also be used. In certain particularly preferred embodiments, $Z^1$ and $Z^2$ together form a moiety derived from D-mannitol. In these embodiments, the boronate ester compound preferably has one of the following structures:

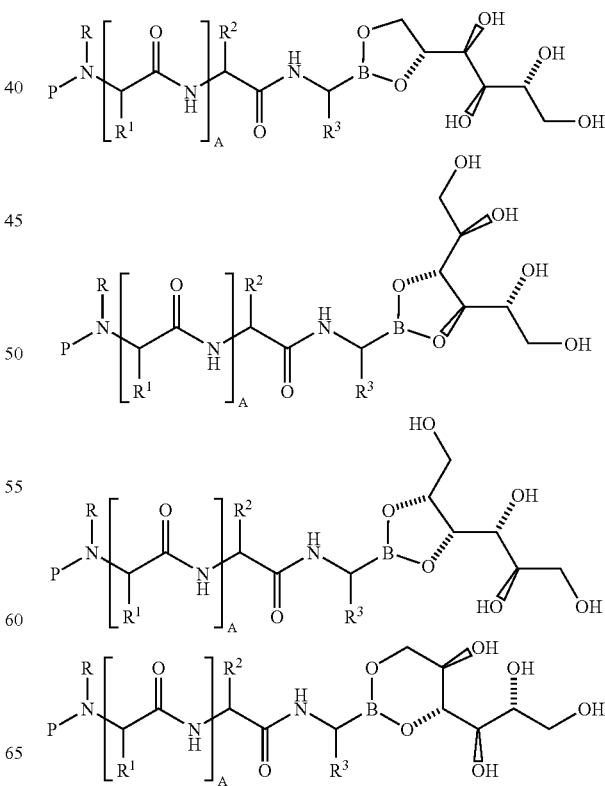

-continued

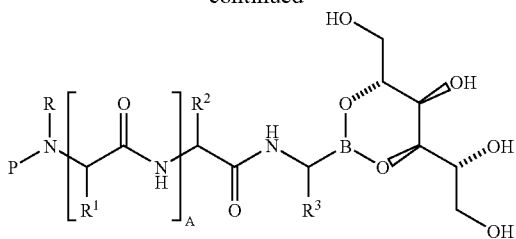

However, structures with larger boronate ester ring sizes are also possible.

In certain particularly preferred embodiments, the boronate ester compound has the following structure:

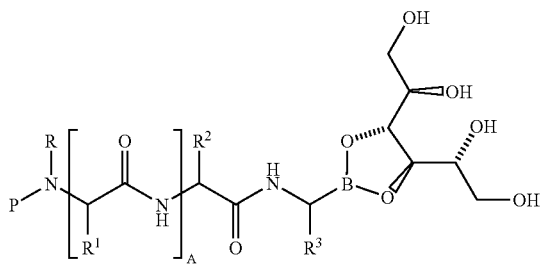

The P moiety of the compound of formula (1) is preferably hydrogen or one of $R^7$—C(O)—, $R^7$—S(O)$_2$—, $R^7$—NH—C(O)—, or $R^7$—O—C(O)—, where $R^7$ is one of alkyl, aryl, alkaryl, or aralkyl, any of which can be optionally substituted, or when Y is $R^7$—C(O)— or $R^7$—S(O)$_2$—, $R^7$ can also be an optionally substituted 5- to 10-membered saturated, partially unsaturated, or aromatic heterocycle.

In certain preferred embodiments, P is one of $R^7$—C(O)— or $R^7$—S(O)$_2$—, and $R^7$ is an optionally substituted 5- to 10-membered saturated, partially unsaturated, or aromatic heterocycle. Preferably, $R^7$ is an aromatic heterocycle, more preferably pyrazinyl, pyridyl, quinolyl, or quinoxalinyl, or a saturated heterocycle, preferably morpholinyl. In some preferred embodiments, P is (2-pyrazine)carbonyl or (2-pyrazine)sulfonyl.

In some preferred embodiments, R is hydrogen. In some other preferred embodiments, R is alkyl, preferably $C_1$–$C_6$ alkyl, more preferably $C_1$–$C_4$ alkyl, and most preferably methyl or ethyl.

The variable A in formula (1) can be 0, 1, or 2. Thus, when A is zero, the residue within the brackets is not present and the boronate ester compound is a dipeptide. Similarly, where A is 1, the residue within the brackets is present and the compound is a tripeptide. Where A is 2, the compound is a tetrapeptide. In certain particularly preferred embodiments, A is zero. For purposes of the invention, the terms "peptide", "dipeptide", and "tripeptide" are intended to encompass compounds comprising natural amino acid residues, unnatural amino acid residues, or a combination of natural and unnatural amino acid residues. It will be apparent from formulae (1)–(3), that the terms "peptide", "dipeptide", and "tripeptide" are used herein to refer to compounds in which the carboxylic acid functionality of the C-terminal amino acid residue is replaced by a boronic acid or boronate ester functionality.

It is preferred that the substituents $R^1$, $R^2$, and $R^3$ in formula (1) are each independently one of hydrogen, $C_1$–$C_8$ alkyl, $C_3$–$C_{10}$ cycloalkyl, or $C_6$–$C_{10}$ aryl, or —CH$_2$—$R^5$, wherein each of $R^1$, $R^2$, $R^3$, and $R^5$ may be optionally substituted. More preferably, $R^1$, $R^2$, and $R^3$ are each independently one of $C_1$–$C_4$ alkyl or —CH$_2$—$R^5$, and $R^5$ is one of cycloalkyl, aryl, heterocyclyl, heteroaryl, or —W—$R^6$ where W is chalcogen and $R^6$ is alkyl. Preferably, $R^5$ is one of $C_6$–$C_{10}$ aryl, ($C_6$–$C_{10}$)ar($C_1$–$C_6$)alkyl, ($C_1$–$C_6$)alk ($C_6$–$C_{10}$)aryl, $C_3$–$C_{10}$ cycloalkyl, $C_1$–$C_8$ alkoxy, or $C_1$–$C_8$ alkylthio or a 5- to 10-membered heteroaryl ring.

In certain preferred embodiments, the compound of formula (1) is one of

D-Mannitol N-(2-pyrazine)carbonyl-L-phenylalanine-L-leucine boronate;

D-Mannitol N-(2-quinoline)sulfonyl-L-homophenylalanine-L-leucine boronate;

D-Mannitol N-(3-pyridine)carbonyl-L-phenylalanine-L-leucine boronate;

D-Mannitol N-(4-morpholine)carbonyl-L-phenylalanine-L-leucine boronate;

D-Mannitol N-(4-morpholine)carbonyl-β-(1-naphthyl)-L-alanine-L-leucine boronate;

D-Mannitol N-(8-quinoline)sulfonyl-β-(1-naphthyl)-L-alanine-L-leucine boronate;

D-Mannitol N-(4-morpholine)carbonyl-(O-benzyl)-L-tyrosine-L-leucine boronate;

D-Mannitol N-(4-morpholine)carbonyl-L-tyrosine-L-leucine boronate; or

D-Mannitol N-(4-morpholine)carbonyl-[O-(2-pyridylmethyl)]-L-tyrosine-L-leucine boronate.

In certain particularly preferred embodiments, the compound of formula (1) is D-Mannitol N-(2-pyrazine)carbonyl-L-phenylalanine-L-leucine boronate, preferably having the following structure:

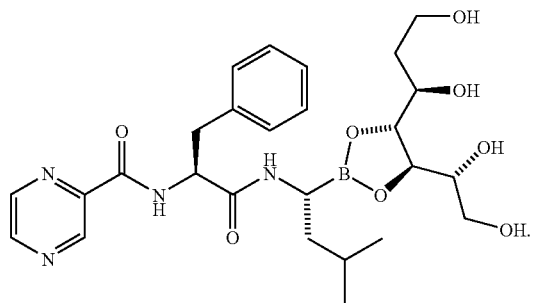

In a second aspect, the invention provides a composition comprising a compound of formula (2):

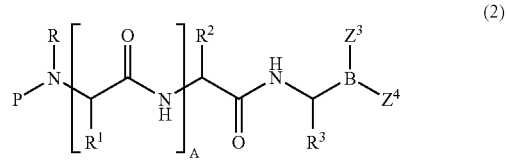

wherein

P is hydrogen or an amino-group-protecting moiety;

R is hydrogen or alkyl;

A is 0, 1, or 2;

$R^1$, $R^2$, and $R^3$ are independently hydrogen, alkyl, cycloalkyl, aryl, or —CH$_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^3$ and $Z^4$ together form a moiety derived from a compound having at least two hydroxyl groups separated by at least two connecting atoms in a chain or ring, said chain or ring comprising carbon atoms and, optionally, a heteroatom or heteroatoms which can be N, S, or O, wherein the atom attached to boron in each case is an oxygen atom;

in a lyophilized powder.

Preferred values for the variables P, R, A, $R^1$, $R^2$, $R^3$, $R^5$, and $R^6$ according to this aspect of the invention are as described above for the first aspect.

The term "moiety derived from a compound having at least two hydroxyl groups" according to this aspect of the invention is used analogously to the term "moiety derived from a sugar" described above, and thus refers to a moiety formed by removing the hydrogen atoms from two hydroxyl groups of a compound having at least two hydroxyl groups. The moiety derived from a compound having at least two hydroxy groups may be attached to boron by the oxygen atoms of any two of its hydroxyl groups. Preferably, the boron atom, the oxygen atoms attached to boron, and the atoms connecting the two oxygen atoms together form a 5- or 6-membered ring. Examples of suitable compounds having at least two hydroxyl groups ("dihydroxy compounds") include, without limitation, pinanediol, pinacol, perfluoropinacol, ethylene glycol, diethylene glycol, catechol, 1,2-cyclohexanediol, 1,3-propanediol, 2,3-butanediol, 1,2-butanediol, 1,4-butanediol, glycerol, and diethanolamine.

For purposes of the present invention, the dihydroxy compound is preferably pharmaceutically acceptable and is preferably miscible or soluble in water or an alcoholic solvent. In some preferred embodiments, the dihydroxy compound is a sugar, as described above, preferably a monosaccharide or disaccharide, more preferably a reduced sugar, and most preferably sorbitol or mannitol. In certain particularly preferred embodiments, the dihydroxy compound is mannitol, most preferably D-mannitol.

The composition according to this aspect of the invention is in the form of a lyophilized powder. In some preferred embodiments, the composition also comprises the free dihydroxy compound. Preferably, the dihydroxy compound and the compound of formula (1) are present in the mixture in a molar ratio ranging from about 0.5:1 to about 100:1, more preferably from about 5:1 to about 100:1. In various embodiments, the dihydroxy compound and the compound of formula (1) are present in a ratio ranging from about 10:1 to about 100:1, from about 20:1 to about 100:1, or from about 40:1 to about 100:1.

In some preferred embodiments, the composition further comprises one or more other pharmaceutically acceptable excipients, carriers, diluents fillers, salts, buffers, stabilizers, solubilizers, and other materials well known in the art. The preparation of pharmaceutically acceptable formulations containing these materials is described in, e.g., *Remington: The Science and Practice of Pharmacy*, 20*th Ed.*, ed. A. Gennaro, Lippincott Williams & Wilkins, 2000.

The compounds and compositions according to the first and second aspects of the invention may be prepared by the methods described herein, or by any method suitable to produce the compound or composition. For example, the boronate esters of formula (1) can be prepared from the corresponding boronic acids by lyophilization in the presence of mannitol or sorbitol, as described herein, or, alternatively, can be prepared from another boronate ester by transesterification. Alternatively, the boronate esters of formula (1) can be prepared by incorporation of the sugar moiety at an earlier stage in the synthesis.

In a third aspect, the invention provides a method for formulating a boronic acid compound, the method comprising:

(a) preparing an aqueous mixture comprising (i) a boronic acid compound; and (ii) a compound having at least two hydroxyl groups separated by at least two connecting atoms in a chain or ring, the chain or ring comprising carbon atoms, and optionally, a heteroatom or heteroatoms which can be N, S, or O; and (b) lyophilizing the mixture.

In certain preferred embodiments, the aqueous mixture comprises one or more co-solvents in addition to water. Preferably, the co-solvent is miscible with water. More preferably, the co-solvent is an alcohol, including, without limitation, ethanol and tert-butanol. The composition of the solvent mixture may range from about 5% to about 95% v/v alcohol. In some embodiments, the aqueous solvent mixture comprises from about 30% to about 50% alcohol, preferably from about 35% to about 45% alcohol. In certain preferred embodiments, the aqueous solvent mixture comprises about 40% tert-butanol.

In some other embodiments, the aqueous solvent mixture comprises from about 1% to about 15% alcohol, preferably from about 5% to about 10% alcohol. In certain preferred embodiments, the aqueous solvent mixture comprises from about 5% to about 10% ethanol.

Preferably, the compound having at least two hydroxyl groups and the boronic acid compound are present in the mixture in a molar ratio ranging from about 1:1 to about 100:1. In various embodiments, the molar ratio of dihydroxy compound to boronic acid compound is about 10:1, 20:1, 30:1, 40:1, 50:1, 60:1, 70:1, 80:1, 90:1, or 100:1. Other ratios are also possible. These ratios are approximate, and may vary somewhat for weighing ease. For example, in the formulation described in Example 1 below, the aqueous mixture contained dihydroxy compound and boronic acid compound in a 10:1 w/w ratio, which corresponds to a 21:1 molar ratio.

The aqueous mixture can be prepared by any order of addition. For example, in some embodiments, the dihydroxy compound is added to an aqueous mixture comprising a boronic acid compound. In some other embodiments, the boronic acid compound is added to an aqueous mixture comprising a dihydroxy compound. In still yet other embodiments, the boronic acid compound and dihydroxy compound can be added at the same time, or nearly at the same time. In some embodiments, it may be advantageous initially to add the boronic acid compound and/or the dihydroxy compound to a solvent mixture containing a higher percentage of co-solvent than is desired for the lyophilization step, and then dilute with water.

In some preferred embodiments, the mixture further comprises one or more pharmaceutically acceptable excipients, carriers, diluents fillers, salts, buffers, stabilizers, solubilizers, and other materials well known in the art. The preparation of pharmaceutically acceptable formulations containing these materials is described in, e.g., *Remington: The Science and Practice of Pharmacy*, 20*th Ed.*, ed. A. Gennaro, Lippincott Williams & Wilkins, 2000.

Preferred compounds having at least two hydroxyl groups ("dihydroxy compounds") according to this aspect of the invention are as described above for the second aspect.

In certain preferred embodiments, the boronic acid compound according to this aspect of the invention has formula (3):

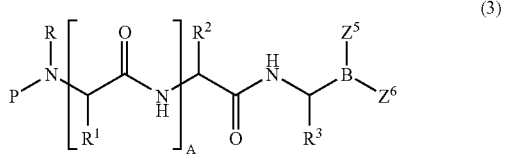

wherein
P is hydrogen or an amino-group-protecting moiety;
R is hydrogen or alkyl;
A is 0, 1, or 2;
$R^1$, $R^2$, and $R^3$ are independently hydrogen, alkyl, cycloalkyl, aryl, or —$CH_2$—$R^5$;
$R^5$, in each instance, is one of aryl, aralkyl, alkaryl, cycloalkyl, heterocyclyl, heteroaryl, or —W—$R^6$, where W is a chalcogen and $R^6$ is alkyl;
where the ring portion of any of said aryl, aralkyl, alkaryl, cycloalkyl, heterocyclyl, or heteroaryl in $R^1$, $R^2$, $R^3$ or $R^5$ can be optionally substituted; and
$Z^5$ and $Z^6$ are each OH.
Preferred values for the variables P, R, A, $R^1$, $R^2$, $R^3$, $R^5$, and $R^6$ according to this aspect of the invention are as described above for the first aspect.
In certain particularly preferred embodiments, the boronic acid compound is one of:
N-(2-pyrazine)carbonyl-L-phenylalanine-L-leucine boronic acid;
N-(2-quinoline)sulfonyl-L-homophenylalanine-L-leucine boronic acid;
N-(3-pyridine)carbonyl-L-phenylalanine-L-leucine boronic acid;
N-(4-morpholine)carbonyl-L-phenylalanine-L-leucine boronic acid;
N-(4-morpholine)carbonyl-β-(1-naphthyl)-L-alanine-L-leucine boronic acid;
N-(8-quinoline)sulfonyl-β-(1-naphthyl)-L-alanine-L-leucine boronic acid;
N-(4-morpholine)carbonyl-(O-benzyl)-L-tyrosine-L-leucine boronic acid;
N-(4-morpholine)carbonyl-L-tyrosine-L-leucine boronic acid; or
N-(4-morpholine)carbonyl-[O-(2-pyridylmethyl)]-L-tyrosine-L-leucine boronic acid.
In a fourth aspect, the invention provides a method for formulating a boronic acid compound, the method comprising:
(a) preparing a boronic acid anhydride compound;
(b) mixing the boronic acid anhydride compound with water and a compound having at least two hydroxyl groups separated by at least two connecting atoms in a chain or ring, the chain or ring comprising carbon atoms, and, optionally, a heteroatom or heteroatoms which can be N, S, or O to produce an aqueous mixture; and
(c) lyophilizing the mixture.
For purposes of the invention, the term "boronic acid anhydride" refers to a chemical compound formed by combination of two or more molecules of a boronic acid compound of formula (3), with loss of one or more water molecules from the boronic acid moieties. When mixed with water, the boronic acid anhydride compound is hydrated to release a free boronic acid compound of formula (3).

In various embodiments, the boronic acid anhydride structure can comprise two, three, four, or more boronic acid units and can have a cyclic or linear configuration. In some embodiments, the boronic acid anhydride compound exists substantially in a single oligomeric form. However, the term "boronic acid anhydride compound" also encompasses mixtures of different oligomeric boronic acid anhydrides.

Non-limiting examples of such oligomeric boronic acid anhydrides are illustrated below:

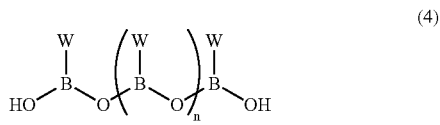

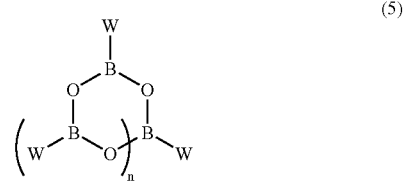

In formulae (4) and (5), n is an integer from 0 to about 10, preferably 0, 1, 2, 3, or 4. W, at each occurrence, preferably has formula (6):

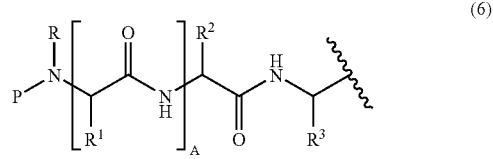

wherein P, R, $R^1$, $R^2$, $R^3$, and A are as defined above for formulae (1)–(3). In some preferred embodiments, the boronic acid anhydride compound comprises a cyclic trimer ("boroxine") of formula (5), wherein n is 1 and W has the meaning given above.

In some embodiments, at least 80% of the boronic acid present in the boronic acid anhydride compound exists in a single oligomeric anhydride form. In some embodiments, at least 85%, 90%, 95%, or 99% of the boronic acid present in the boronic acid anhydride compound exists in a single oligomeric anhydride form. In some embodiments, the boronic acid anhydride compound consists essentially of a single oligomeric boronic acid anhydride. In some embodiments, the boronic acid anhydride compound consists of a single oligomeric boronic acid anhydride.

In some preferred embodiments, the boronic acid anhydride compound consists of, or consists essentially of, a boroxine of formula (5), wherein n is 1, and W has the meaning given above. In certain particularly preferred embodiments, the boronic acid anhydride compound consists of, or consists essentially of, a boroxine having formula (7):

(7)

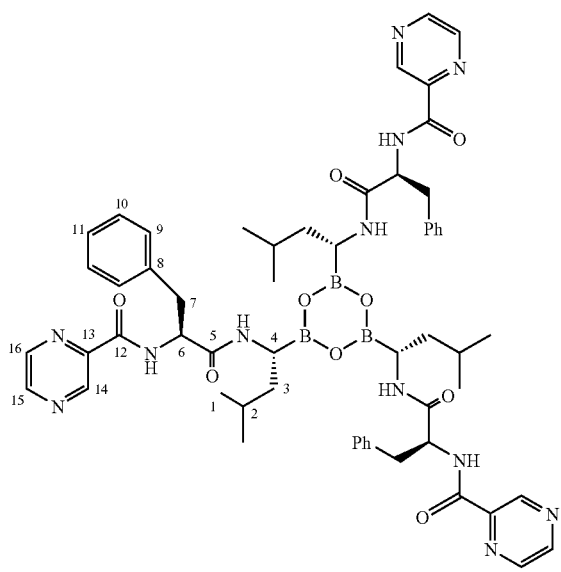

The boronic acid anhydride compound preferably can be prepared from the corresponding boronic acid compound of formula (3) by exposure to dehydrating conditions, including, but not limited to, recrystallization, lyophilization, exposure to heat, and/or exposure to a drying agent. Nonlimiting examples of suitable recrystallization solvents include ethyl acetate, dichloromethane, hexanes, ether, acetonitrile, ethanol, and mixtures thereof.

In a fifth aspect, the invention provides compositions prepared according to the methods of the third or fourth aspects of the invention. In some preferred embodiments, formulation of a boronic acid according to the methods of the invention results in formation of a chemical derivative of the boronic acid compound, preferably formation of a boronate ester. In these embodiments, formulation of a boronic acid compound according to the method of the invention produces a composition comprising a boronate ester compound, according to the second aspect of the invention.

In some other embodiments, formulation of a boronic acid compound according to the method of the invention does not result in formation of a chemical derivative of the boronic acid compound. In these embodiments, the composition according to the fifth aspect of the invention comprises a boronic acid compound and a compound having at least two hydroxyl groups in a lyophilized powder.

The compositions according to the second and fifth aspects of the invention can be readily reconstituted by adding an aqueous solvent. Preferably, the reconstitution solvent is suitable for pharmaceutical administration. Examples of suitable reconstitution solvents include, without limitation, water, saline, and phosphate buffered saline (PBS). For clinical use, the compositions according to the second or fifth aspects of the invention are preferably reconstituted with sterile saline (0.9% w/v).

Upon reconstitution in aqueous medium, an equilibrium is established between any boronate ester present in the composition and the corresponding boronic acid. Typically, equilibrium is reached quickly, e.g., within 10–15 minutes, after the addition of water. The relative concentrations of boronate ester and boronic acid present at equilibrium is dependent upon the pH of the solution, temperature, and the ratio of dihydroxy compound to boronic acid compound.

In a sixth aspect, the invention provides a boronic acid anhydride compound useful for the methods of the invention. Preferred boronic acid anhydride compounds are as described above for the fourth aspect of the invention. When mixed with water, the boronic acid anhydride compound is hydrated to release the free boronic acid.

The following examples are intended to further illustrate certain preferred embodiments of the invention, and are not intended to limit the scope of the invention.

EXAMPLES

Example 1

Preparation of a Lyophilized Formulation of N-(2-pyrazine)-carbonyl-L-phenylalanine-L-leucine boronic acid with D-mannitol Approximately 40 mg of N-(2-pyrazine)carbonyl-L-phenylalanine-L-leucine boronic acid was weighed into a container, and 16 mL of tert-butanol was added. The container was closed and the suspension was warmed to approximately 45° C. for 5 minutes to complete dissolution of the compound. Water (24 mL) was added with stirring, followed by 0.4 g of mannitol, added as an excipient, 1% w/v. The mixture was stirred to complete dissolution and then cooled to ambient temperature. The solution was filtered through a 0.45 μm nylon membrane. One milliliter aliquots were placed in 5 mL serum bottles. Split rubber stoppers were partially inserted into the bottles, and the bottles were placed in a freeze dryer with a shelf temperature of −45° C. After approximately 1 hour, the vacuum was applied. The shelf temperature was allowed to rise gradually to −35° C. and maintained at −35° C. until the ice was gone from the samples (approximately 40 hours). The shelf temperature control was then turned off and the shelf temperature was allowed to gradually rise to 0° C. A secondary drying cycle was carried out by increasing the shelf temperature in 3 increments to 25° C. over a time period of 1.5 hours. The shelf temperature was maintained at 25° C. for 2 hours. The samples were sealed under nitrogen and removed from the freeze dryer.

The residual moisture content of the samples was determined by Karl Fischer analysis, using three lyophilized products. The water content was 0.88% by weight.

Fast Atom Bombardment (FAB) mass spectral analysis of the lyophilized product showed a strong signal at m/z=531 (see Figure), indicative of formation of a covalent boronate ester adduct between N-(2-pyrazine)carbonyl-L-phenylalanine-L-leucine boronic acid and D-mannitol. Glycerol was employed as the matrix, and a signal for the glycerol adduct with N-(2-pyrazine)carbonyl-L-phenylalanine-L-leucine boronic acid was observed at m/z=441. However, the intensity of the signal at m/z=441 was very low compared to the signal at m/z=531, possibly indicative of the enhanced stability of the D-mannitol adduct.

Example 2

Production-Scale Preparation of a Lyophilized Formulation of N-(2-pyrazine)carbonyl-L-phenylalanine-L-leucine boronic acid with D-Mannitol In a dean compounding vessel, a solution of 97% tert-butanol/3% Water for Injection was prepared by warming the required amount of tert-butanol to 35° C. and adding Water for Injection. Approximately 5% of the solution was reserved for use in rinsing. The solution was cooled to 15–30° C., and N-(2-pyrazine)carbonyl-L-phenylalanine-L-leucine boroxine was added with stirring. The container was rinsed with the reserved tert-butanol/water solution, and the rinses were added to the main vessel. The mixture was stirred until the boronic acid compound was completely dissolved. Mannitol was added, with residual mannitol being rinsed into the reaction vessel with fresh Water for Injection. Sufficient Water for Injection was added to reduce the total alcohol content to 40% v/v. The mixture was stirred until the mannitol was completely dissolved. The mixture was filtered through a 0.22 micron filter. Aliquots of the filtered solution were placed into previously sterilized vials. The vials were sealed with lyophilization stoppers and were placed on lyophilizer chamber shelves maintained at −45° C. After two hours, the freeze dryer chamber was evacuated and the chamber pressure was adjusted to 100–200 microns with sterile nitrogen. The lyophilizer chamber shelves were warmed to −30° C. using an appropriate ramp rate, and held at that temperature for 10–15 hours. After each of the product thermocouples read −33° C. or warmer, the shelf temperature was adjusted to −15° C. over 7 hours using an appropriate ramp rate and maintained at that temperature for 5 hours. After all product thermocouples recorded the shelf temperature, the shelf was warmed to 0° C. over a period of at least 7 hours using an appropriate ramp rate. When all thermocouples recorded 0° C., the shelf was warmed to 27° C. and maintained at that temperature for 4 hours. At the end of the terminal drying phase, the chamber pressure was restored using sterile nitrogen, and the vials were sealed and removed.

The mannitol boronate structure was confirmed by mass spectrometry (positive ion or electrospray, acetonitrile solution) and $^{13}$C NMR.

The $^{13}$C NMR (d$_6$-DMSO) spectrum revealed three new mannitol carbon signals, as compared with the same region of the spectrum for free mannitol. This result indicates formation of a symmetrical mannitol complex as illustrated below:

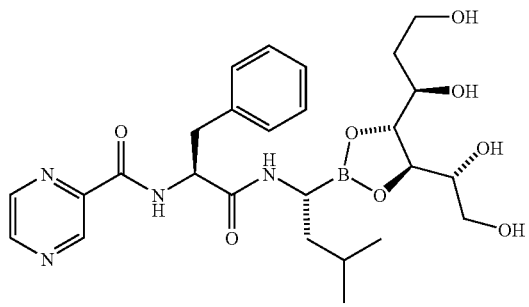

Example 3

Preparation of N-(2-pyrazine)carbonyl-L-phenylalanine-L-leucine boroxine (1S,2S,3R,5S)-Pinanediol N-(2-pyrazine)carbonyl-L-phenylalanine-L-leucine boronate was synthesized according to the procedures described in Adams et al., U.S. Pat. No. 5,780,454 (1998) and dissolved in a mixture of methanol and hexanes at room temperature. Liberation of the terminal boronic acid sub-unit from the pinanediol protecting group was effected by treatment with 2-methylpropaneboronic acid and aqueous hydrochloric acid in methanol and hexanes at room temperature. The progress of the reaction was assessed by thin layer chromatography. The reaction mixture was partitioned with hexanes/methanol and the aqueous methanol layer was concentrated to afford a solid. The solid was reconstituted with aqueous sodium hydroxide. After washing with dichloromethane, the aqueous layer was acidified with aqueous hydrochloric acid. The product was extracted using dichloromethane. After drying with magnesium sulfate, the batch was filtered and the dichloromethane was removed under reduced pressure. Hexanes were added and crude product was isolated by further stripping of solvent. The product was recrystallized from ethyl acetate, collected by filtration and dried under vacuum at 65–70° C. When the material was dry, it was packaged in amber glass bottles with teflon-lined caps, labeled, and stored at −20° C.

The product has the trimeric boroxine structure shown below, as supported by the results of mass spectrometry, $^1$H NMR, and elemental analysis.

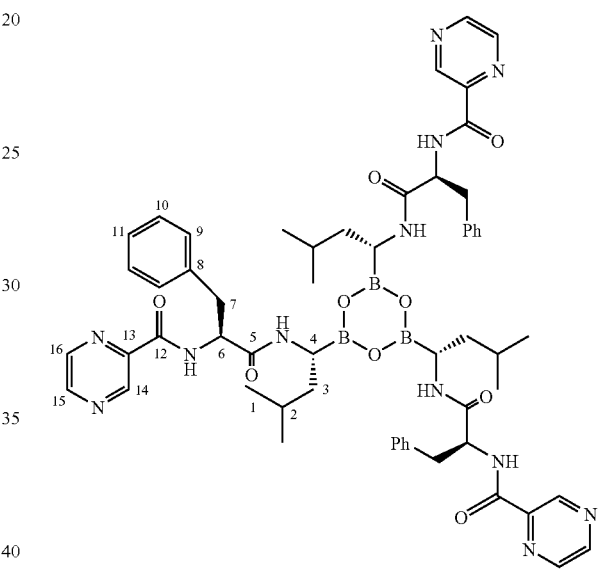

Mass spectral analysis (positive ion, electrospray) of an acetonitrile solution of the product exhibited sodium, proton, and potassium adducts of trimeric boroxine at m/z=1121, 1099, and 1137, respectively. No monomeric boronic acid was observed in any adduct form.

The $^1$H NMR (d$_6$-DMSO) spectrum showed no BOH resonance, suggesting the presence of the boroxine structure.

X-ray powder diffraction and polarized-light microscopy analysis demonstrated the crystalline nature of the product, and dynamic vapor sorption studies demonstrated its non-hygroscopic nature, consistent with the anhydride structure.

Example 3

Reconstitution of N-(2-pyrazine)carbonyl-L-phenylalanine-L-leucine boronic acid

The lyophilized formulation of N-(2-pyrazine)carbonyl-L-phenylalanine-L-leucine boronic acid with D-mannitol was prepared as described in Example 1. One sample was reconstituted with 2 mL of water. Dissolution was complete within 1–2 minutes of shaking. The entire solution was transferred to a volumetric flask, diluted, and analyzed by HPLC for content of N-(2-pyrazine)carbonyl-L-phenylalanine-L-leucine boronic acid. The total drug content was 1.09 mg. A second sample was reconstituted with 1 mL of propylene glycol:EtOH:H$_2$O, 40:10:50. Dissolution was complete with 1 minute of shaking. The total drug content was 1.11 mg.

The lyophilized formulation was also reconstituted with 0.9% w/v saline. The lyophilized material dissolved readily at concentrations up to 6 mg/mL. By contrast, solid N-(2-pyrazine)carbonyl-L-phenylalanine-L-leucine boronic acid was not soluble in 0.9% w/v saline at a concentration of 1 mg/mL.

To be certain that free N-(2-pyrazine)carbonyl-L-phenylalanine-L-leucine boronic acid was rapidly liberated upon reconstitution of the lyophilized formulation in aqueous solution, the lyophilized formulation was dissolved in neat DMSO and assayed for inhibition of the chymotrypsin-like activity of the 20S proteasome as described in U.S. Pat. No. 5,780,454. Proteasome inhibition can only be observed if hydrolysis under the assay conditions is fast. The observed K$_i$ value of 0.3 nM is equivalent to that observed for free N-(2-pyrazine)carbonyl-L-phenylalanine-L-leucine boronic acid, indicating complete and rapid hydrolysis of the D-mannitol adduct under the assay conditions.

Example 4

HPLC Analysis of N-(2-pyrazine)carbonyl-L-phenylalanine-L-leucine boronic acid

| System parameters: | |
|---|---|
| Column: | Adsorbosphere-HS-C18, 5µ, 250 × 4.6 mm |
| Mobile Phase: | 65/35: methanol/water containing 0.1% TFA |
| Flow Rate: | 1.0 mL/min |
| Detection/Sensitivity: | PDA and UV at 255 nm, 0.1 aufs |
| Injection volume: | 25 µL |
| Internal Standard Solution: | 0.18 mg/mL diphenylamine in methanol |
| Sample Preparation: | Accurately weighed 0.5–1.5 mg portions of the sample or reference standard were dissolved in 2.00 mL of the internal standard solution. |

Chromatographic parameters:

| | Sample | Internal Standard |
|---|---|---|
| Retention time | 8.4 min | 18.9 min |
| Capacity factor, k' | 2.0 | 5.8 |
| Asymmetry (10%) | 1.7 | 1.3 |
| Rel. Retention, α | | 0.34 |
| Resolution, R$_s$ = ΔT/ΣW$_{1/2}$ | | 15.1 |

ΔT and ΣW$_{1/2}$ are, respectively, the differences in retention times and the sum of the mid-width of the sample and internal standard peaks. Minor variation of the mobile phase is allowed to achieve results similar to those above.

Example 5

Stability of Formulations

Solid N-(2-pyrazine)carbonyl-L-phenylalanine-L-leucine boronic acid

N-(2-pyrazine)carbonyl-L-phenylalanine-L-leucine boronic acid was prepared as described in U.S. Pat. No. 5,780,454. The product was obtained as a white amorphous powder. The product was stable for more than 2 years when stored at −20° C., as determined by HPLC analysis (purity >97%). When stored at 2–8° C., the product was not stable for longer than 3–6 months.

Liquid N-(2-pyrazine)carbonyl-L-phenylalanine-L-leucine boronic acid

A sterile liquid formulation (0.5 mg/mL) of N-(2-pyrazine)carbonyl-L-phenylalanine-L-leucine boronic acid was prepared in 0.9% w/v saline, 2% v/v ethanol and 0.1% w/v ascorbic acid. When stored at 2–8° C., the liquid formulation was not stable for longer than 6 months, as determined by HPLC analysis.

Lyophilized D-mannitol N-(2-pyrazine)carbonyl-L-phenylalanine-L-leucine boronate The lyophilized product was prepared according to Example 1 and stored at 5° C., ambient temperature, 37° C., and 50° C. Stability was monitored for approximately 18 months by periodically reconstituting a sample and analyzing the entire contents of the bottle by HPLC. Over this time period, there was no loss of drug in the lyophilized product stored at any temperature and no evidence of degradation product peaks in the HPLC chromatograms.

Reconstituted solution of N-(2-pyrazine)carbonyl-L-phenylalanine-L-leucine boronic acid The lyophilized product was prepared according to Example 1, and samples (2.5 mg/vial) were reconstituted with 2.5 mL of 0.9% w/v sterile saline. Dissolution was complete within 10 seconds and afforded a clear colorless solution containing 1 mg/mL of N-(2-pyrazine)carbonyl-L-phenylalanine-L-leucine boronic acid. The solution showed no sign of degradation when stored at ambient temperature (23° C.) for 43 hours. No special care was taken to protect the solution from light.

What is claimed is:

1. A method for formulating a boronic acid compound, the method comprising:
   (a) preparing an aqueous mixture comprising
      (i) a boronic acid compound; and
      (ii) a compound selected from the group consisting of pinanediol, pinacol, perfluoropinacol, ethylene glycol, diethylene glycol, catechol, 1,2-cyclohexanediol, 1,3-propanediol, 2,3-butanediol, 1,2-butanediol, 1,4-butanediol, glycerol, and diethanolamine; and
   (b) lyophilizing the mixture.

2. The method of claim 1, wherein the boronic acid compound has formula (3):

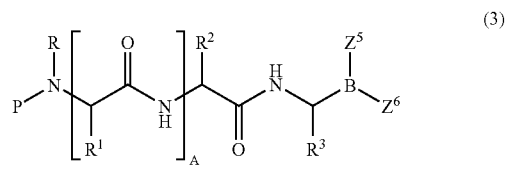

(3)

wherein:

P is hydrogen or an amino-group-protecting moiety;

R is hydrogen or alkyl;

A is 0, 1, or 2;

R$^1$, R$^2$, and R$^3$ are independently hydrogen, alkyl, cycloalkyl, aryl, or —CH$_2$—R$^5$;

R$^5$, in each instance, is one of aryl, aralkyl, alkaryl, cycloalkyl, heterocyclyl, heteroaryl, or —W—R$^6$, where W is a chalcogen and R$^6$ is alkyl;

where the ring portion of any of said aryl, aralkyl, alkaryl, cycloalkyl, heterocyclyl, or heteroaryl in R$^1$, R$^2$, R$^3$ or R$^5$ can be optionally substituted; and Z$^5$ and Z$^6$ are each OH.

3. The method of claim 2, wherein P is one of R$^7$—C(O)—, R$^7$—S(O)$_2$, R$^7$—NH—C(O)—, or R$^7$—O—C(O)—;

where R$^7$ is one of alkyl, aryl, alkaryl, or aralkyl, any of which can be optionally substituted, or when P is R$^7$—C(O)— or R$^7$—S(O)$_2$—, R$^7$ can also be an optionally substituted 5- to 10-membered saturated, partially unsaturated, or aromatic heterocycle.

4. The method of claim 3, wherein P is $R^7$—C(O)— or $R^7$—S(O)$_2$—, and $R^7$ is an aromatic heterocycle.

5. The method of claim 4, wherein P is (2-pyrazine)carbonyl or (2-pyrazine)sulfonyl.

6. The method of claim 3, wherein:

A is zero;

R is hydrogen or $C_1$–$C_8$ alkyl; and $R^3$ is $C_1$–$C_6$ alkyl.

7. The method of claim 6, wherein P is (2-pyrazine)carbonyl or (2-pyrazine)sulfonyl.

8. The method of claim 3, wherein:

$R^1$, $R^2$ and $R^3$ are each independently one of hydrogen, $C_1$–$C_8$ alkyl, $C_3$–$C_{10}$ cycloalkyl, or $C_8$–$C_{10}$ aryl, or —CH$_2$—$R^5$;

$R^5$, in each instance, is one of $C_6$–$C_{10}$ aryl, ($C_6$–$C_{10}$)ar($C_1$–$C_6$)alkyl, ($C_1$–$C_6$)alk($C_6$–$C_{10}$)aryl, $C_3$–$C_{10}$ cycloalkyl, $C_1$–$C_8$ alkoxy, or $C_1$–$C_8$ alkylthio;

where the ring portion of any of said aryl, aralkyl, alkaryl, cycloalkyl, heterocyclyl, or heteroaryl groups of $R^1$, $R^2$, $R^3$ or $R^5$ can be optionally substituted.

9. The method of claim 1, wherein the boronic acid compound is:

N-(2-pyrazine)carbonyl-L-phenylalanine-L-leucine boronic acid;

N-(2-quinoline)sulfonyl-L-homophenylalanine-L-leucine boronic acid;

N-(3-pyridine)carbonyl-L-phenylalanine-L-leucine boronic acid;

N-(4-morpholine)carbonyl-L-phenylalanine-L-leucine boronic acid;

N-(4-morpholine)carbonyl-β-(1-naphthyl)-L-alanine-L-leucine boronic acid;

N-(8-quinoline)sulfonyl-β-(1-naphthyl)-L-alanine-L-leucine boronic acid;

N-(4-morpholine)carbonyl-(O-benzyl)-L-tyrosine-L-leucine boronic acid;

N-(4-morpholine)carbonyl-L-tyrosine-L-leucine boronic acid; or

N-(4-morpholine)carbonyl-[O-(2-pyridylmethyl)]-L-tyrosine-L-leucine boronic acid.

10. The method of claim 1, wherein the boronic acid compound is N-(2-pyrazine)carbonyl-L-phenylalanine-L-leucine boronic acid.

11. The method of claim 1, wherein the aqueous mixture further comprises a water-miscible co-solvent.

12. The method of claim 11, wherein the water-miscible co-solvent is an alcohol.

* * * * *